United States Patent
Stoffel et al.

(10) Patent No.: US 8,109,935 B2
(45) Date of Patent: Feb. 7, 2012

(54) IMPLANT INSERTER DEVICE

(75) Inventors: Florence H. Stoffel, Whitehouse Station, NJ (US); Karl Dallas Kirk, III, New York, NY (US); Paul J. Mulhauser, New York, NY (US); Lyndon Thomas Treacy, Long Island City, NY (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 366 days.

(21) Appl. No.: 12/466,564

(22) Filed: May 15, 2009

(65) Prior Publication Data

US 2010/0292704 A1 Nov. 18, 2010

(51) Int. Cl.
*A61B 17/58* (2006.01)
(52) U.S. Cl. .......................................................... 606/99
(58) Field of Classification Search ...................... 606/99
See application file for complete search history.

(56) References Cited

U.S. PATENT DOCUMENTS

| | | | |
|---|---|---|---|
| 2,532,972 A * | 12/1950 | Vertin | 81/443 |
| 3,875,595 A | 4/1975 | Froning | |
| 4,785,826 A * | 11/1988 | Ward | 600/567 |
| 4,877,020 A * | 10/1989 | Vich | 606/86 R |
| 4,934,363 A | 6/1990 | Smith et al. | |
| 4,946,468 A | 8/1990 | Li | |
| 5,496,328 A | 3/1996 | Nakajima et al. | |
| 5,662,658 A | 9/1997 | Wenstrom, Jr. | |
| 5,688,276 A | 11/1997 | Shaffer | |
| 5,782,830 A | 7/1998 | Farris | |
| 6,066,174 A | 5/2000 | Farris | |
| 6,171,310 B1 | 1/2001 | Giordano et al. | |
| 6,319,257 B1 | 11/2001 | Carignan et al. | |
| 6,440,142 B1 | 8/2002 | Ralph et al. | |
| 6,610,065 B1 | 8/2003 | Branch et al. | |
| 6,663,638 B2 | 12/2003 | Ralph et al. | |
| 6,866,668 B2 * | 3/2005 | Giannetti et al. | 606/99 |
| 7,156,880 B2 | 1/2007 | Evans et al. | |
| 7,166,133 B2 | 1/2007 | Evans et al. | |
| 7,235,107 B2 | 6/2007 | Evans et al. | |
| 7,241,316 B2 | 7/2007 | Evans et al. | |
| 7,276,081 B1 | 10/2007 | Coates et al. | |
| 7,857,840 B2 * | 12/2010 | Krebs et al. | 606/327 |
| 7,918,858 B2 * | 4/2011 | Stad et al. | 606/86 A |
| 2004/0138758 A1 | 7/2004 | Evans et al. | |
| 2004/0193154 A1 | 9/2004 | Leatherbury et al. | |
| 2004/0267277 A1 | 12/2004 | Zannis et al. | |
| 2005/0129668 A1 | 6/2005 | Giannetti et al. | |
| 2005/0137600 A1 | 6/2005 | Jacobs et al. | |
| 2006/0178748 A1 | 8/2006 | Dinger, III et al. | |

(Continued)

*Primary Examiner* — Thomas J Sweet
*Assistant Examiner* — Christopher D Prone
(74) *Attorney, Agent, or Firm* — Greenberg Traurig, LLP

(57) ABSTRACT

An implant inserter device having an outer collar, an inner sleeve slidably and rotatably received within the outer collar, and a push rod slidably received within the inner sleeve. The outer collar has at least one cammed surface formed on an interior surface thereof, while the inner sleeve has at least one rib projecting outwardly from an exterior surface thereof. The rib is releasably engageable with the cammed surface when the inner sleeve is rotated relative to the outer collar. As a result, a distal end of the inner sleeve collapses from an undeformed position, in which the inner sleeve does not grip an implant housed therein, and a deformed position, in which the inner sleeve grips the implant. The push rod is movable between an extended position and a retracted position for urging the implant through and from the inner sleeve for insertion into a defect in damaged cartilage and bone.

17 Claims, 21 Drawing Sheets

U.S. PATENT DOCUMENTS

| | | |
|---|---|---|
| 2007/0043376 A1* | 2/2007 | Leatherbury et al. .......... 606/99 |
| 2008/0015709 A1 | 1/2008 | Evans et al. |
| 2008/0039849 A1 | 2/2008 | Briest |
| 2008/0071279 A1 | 3/2008 | Bandeira et al. |
| 2008/0195115 A1 | 8/2008 | Oren et al. |
| 2009/0030528 A1 | 1/2009 | Evans et al. |
| 2009/0043400 A1 | 2/2009 | Evans et al. |

* cited by examiner

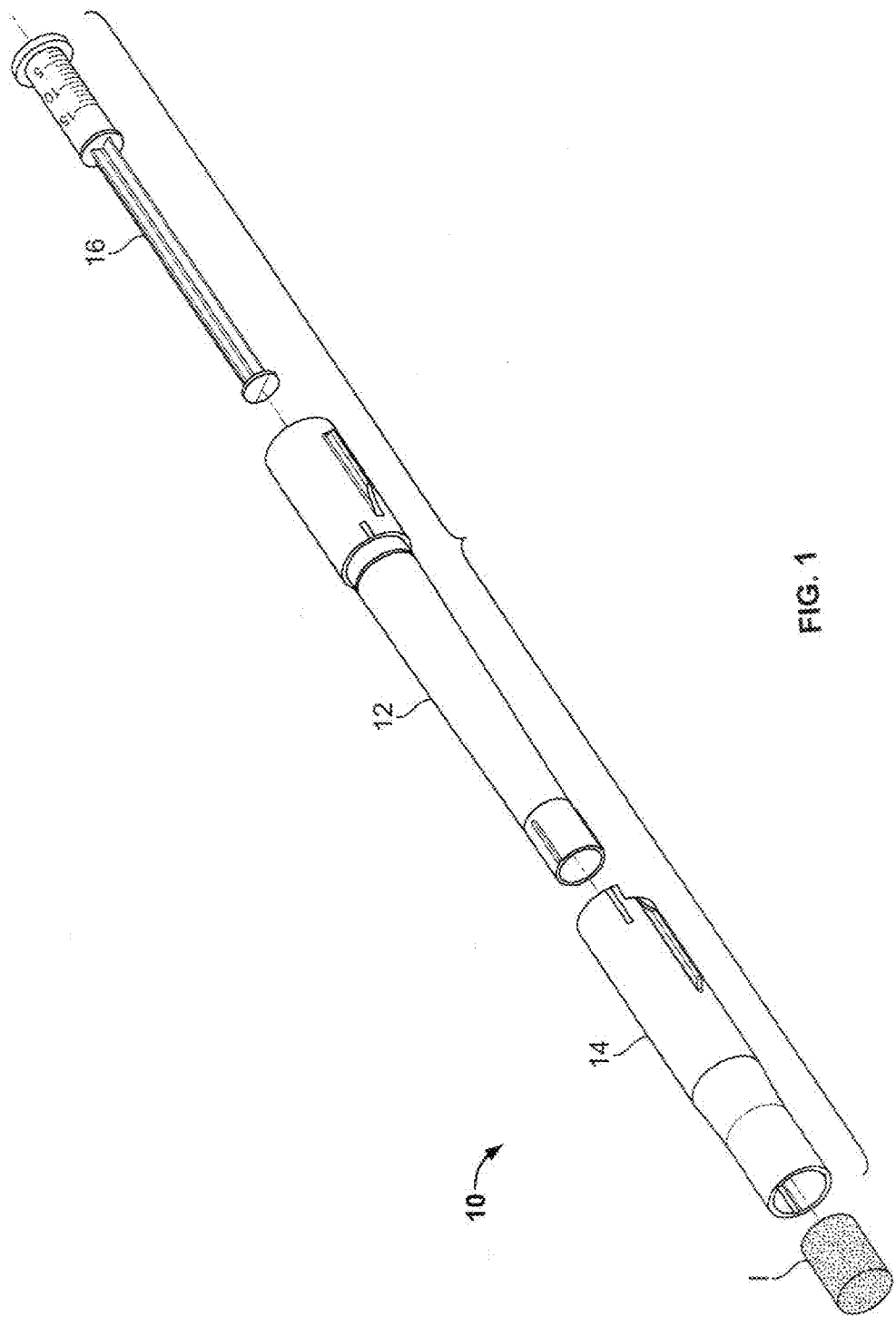

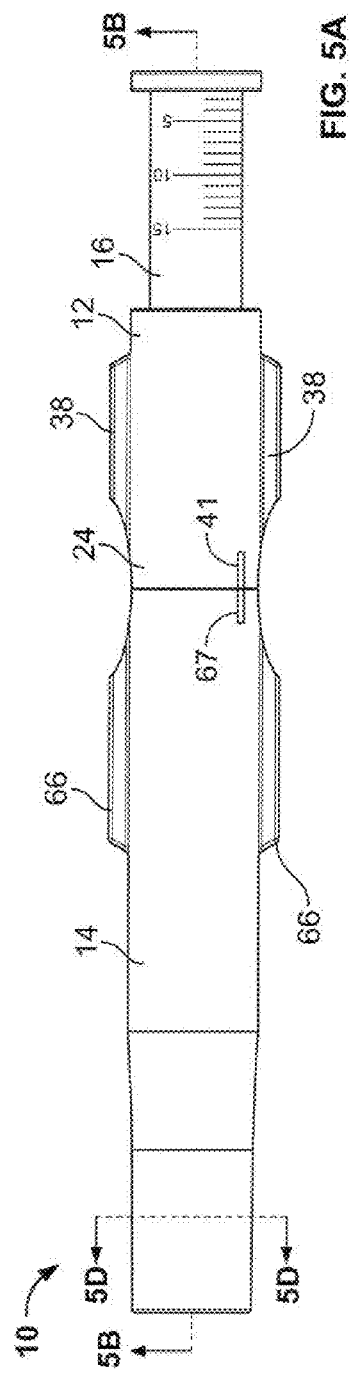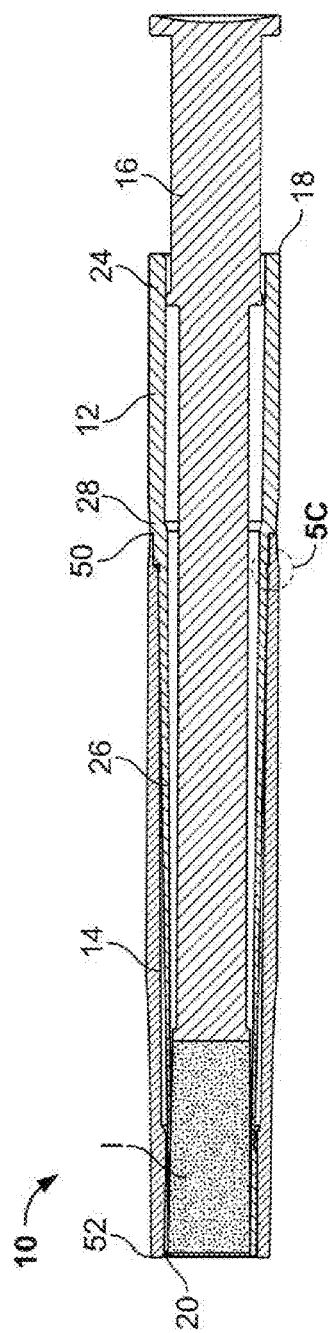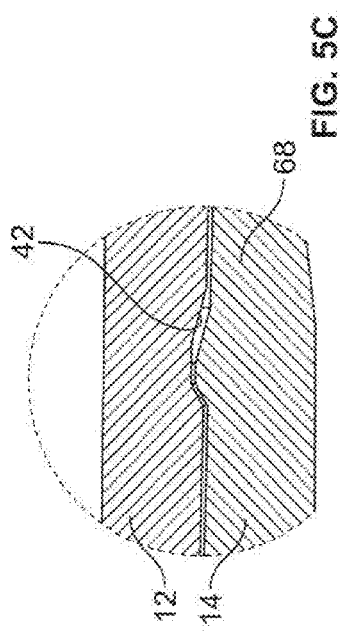

IMPLANT INSERTER DEVICE

FIELD OF THE INVENTION

The present invention relates to a surgical instrument and, more particularly, to an implant inserter device for use in connection with surgical repair of damaged articular cartilage and bone.

BACKGROUND OF THE INVENTION

Damage to articular cartilage can result from a variety of causes, such as sports injuries, accidents, or wear and tear over time. There are several surgical procedures utilized for repairing articular cartilage damage. One surgical procedure includes the use of osteochondral autograft and allograft implants to repair the damaged cartilage. When the procedure necessitates the use of osteochondral autograft implants, the damaged section of cartilage and bone is removed from the joint at issue, and a new, healthy implant of bone with its cartilage covering is punched out of the same joint and replanted into the hole remaining from the removal of the damaged cartilage and bone. When the procedure contemplates the use of osteochondral allograft implants, the implants are taken from deceased donors, or the implants may be processed and manufactured from human bone and tissue.

An implant inserter device is a crucial surgical instrument utilized during cartilage and bone repair procedures. The main purpose and function of an implant inserter device is to insert the implant into the hole remaining from the removal of the damaged cartilage and bone. The implant must be positioned and inserted into the hole precisely, otherwise the damage would not be repaired and heal properly. Consequently, it is important for a surgeon to have at her disposal a reliable implant delivery device that firmly retains the implant, while providing her with full and complete control of the implant during the insertion procedure. Moreover, the implant inserter device must firmly retain the implant in order for the surgeon to measure, cut and trim the implant to its correct size prior to insertion. What is needed, therefore, is an implant inserter device that sufficiently retains an implant, while enabling a surgeon to have full and complete control of the implant throughout the entire surgical procedure.

SUMMARY OF THE INVENTION

The present invention overcomes the disadvantages and shortcomings of the prior art discussed above by providing a new and improved implant inserter device. The implant inserter device includes an outer collar, an inner sleeve slidably and rotatably received within the outer collar, and a push rod slidably received within the inner sleeve. The outer collar has at least one cammed surface formed on an interior surface thereof, while the inner sleeve has at least one rib projecting outwardly from an exterior surface thereof. The rib is releasably engageable with the cammed surface when the inner sleeve is rotated relative to the outer collar. As a result, a distal end of the inner sleeve, which is made from a soft and flexible material, collapses from an undeformed position, in which the inner sleeve does not grip an implant housed therein, and a deformed position, in which the inner sleeve grips the implant. The push rod is movable between an extended position and a retracted position for urging the implant through and from the inner sleeve for insertion into a defect in damaged cartilage and bone.

In accordance with another aspect of the present invention, a miter cap is removably attached to the implant inserter device. The miter cap includes a tubular shaft that is sized and shaped to removably receive the outer collar of the implant inserter device, and an aperture that is substantially aligned with the inner sleeve of the implant inserter device. When the push rod is moved to its said extended position, at least a portion of the implant may be urged through the aperture of the miter cap and extends outwardly therefrom. This enables the implant to be trimmed to a desired length. The thickness of the miter cap is automatically included in establishing the length of the implant when using the indicia imprinted on the push rod.

Specifically, the present invention has been adapted for use for the surgical repair of damaged articular cartilage and bone. However, the present invention can be utilized in connection with any applicable surgical procedures (e.g., spinal disc surgery, etc.). Further features and advantages of the invention will appear more clearly on a reading of the detailed description of an exemplary embodiment of the invention, which is given below by way of example only with reference to the accompanying drawings.

BRIEF DESCRIPTION OF THE DRAWINGS

Reference is made to the following detailed description of the exemplary embodiment considered in conjunction with the accompanying drawings, in which:

FIG. 1 is an exploded perspective view, looking from the top, of an implant inserter device constructed in accordance with an exemplary embodiment of the present invention;

FIG. 5A is a side elevational view of the implant inserter device illustrated in FIG. 1, with the device shown as fully assembled;

FIG. 5B is a cross-sectional view, taken along section line 5B-5B and looking in the direction of the arrows, of the implant inserter device illustrated in FIG. 5A;

FIG. 5C is an enlarged cross-sectional view showing detail 5C from FIG. 5B;

DETAILED DESCRIPTION OF THE EXEMPLARY EMBODIMENT

Figure 2A:
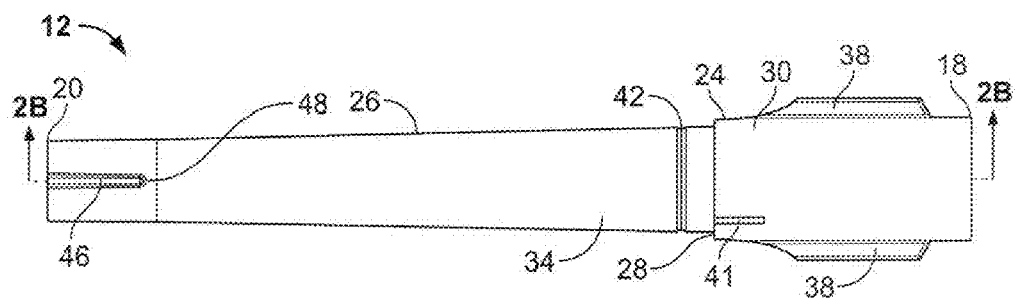
FIG. 2A is a side elevational view of an inner sleeve utilized by the implant inserter device illustrated in FIG. 1.
Figure 2B:
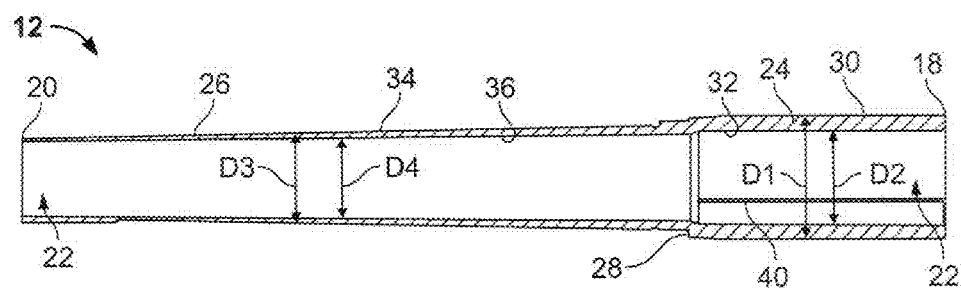
FIG. 2B is a cross-sectional view, taken along section line 2B-2B and looking in the direction of the arrows, of the inner sleeve illustrated in FIG. 2A.
Figure 2C:
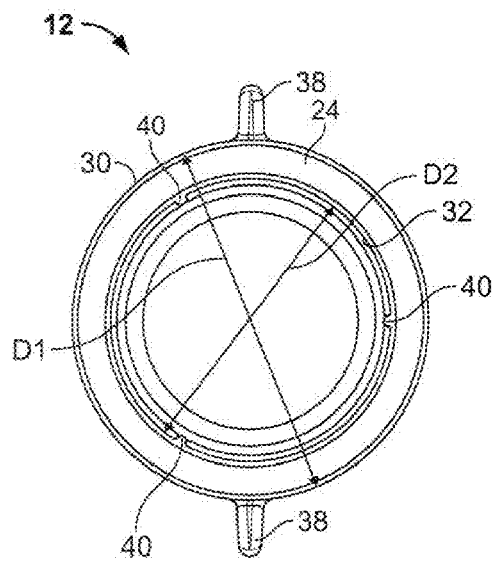
FIG. 2C is front elevational view of a distal end of the inner sleeve illustrated in FIG. 2A.

Referring to FIG. 1, an implant inserter device 10 includes a tubular-shaped inner sleeve 12, a tubular-shaped outer collar 14, and an elongated push rod 16. The inner sleeve 12 and the outer collar 14, whose features and functions shall be described in greater detail hereinafter, are coupled with one another and cooperate to house and retain a surgical implant I. The push rod 16, whose features and function shall be described in greater detail hereinafter, is inserted into the inner sleeve 12, and controls the position of the implant I within the inner sleeve 12, as well as facilitates the insertion of the implant I into a cartilage and bone defect site (not shown in FIG. 1). As used herein to describe an element of the implant inserter device 10 (such as the inner sleeve 12, the outer collar 14, and the push rod 16), the term "proximal" means closest to a user (e.g., surgeon, etc.) of the device 10 and farthest from the surgical site (e.g., the defect). As used herein, the term "distal" means farthest from the user and closest to the surgical site.

The implant I may consist of any type of human bone and/or tissue suitable for the repair of a cartilage and bone defect, such as, for example, an osteochondral autograft or an osteochondral allograft. More particularly, the implant I may consist of an allograft that is processed from human bone and tissue, such as, for example, an allograft-based multi-component cancellous scaffold plug. Examples of allograft plug implants suitable for use with the implant inserter device 10 are provided in (1) U.S. application Ser. Nos. 10/438,883; 11/151,270; and 12/179,034 for "Cartilage Allograft Plug; and (2) Ser. No. 10/815,778 for "Cartilage Implant Assembly and Method for Implantation," while examples of allograft cancellous construct implants are provided in (1) U.S. application Ser. No. 11/657,042 for "Two Piece Cancellous Construct for Cartilage Repair"; and (2) Ser. No. 12/043,001 for "Cancellous Construct with Support Ring for Repair of Osteochondral Defects." The implant I may also be constructed from a synthetic material or a xenograft material. The implant I is generally cylindrical in shape, but it may consist of other shapes and sizes that are suitable for repairing a specific cartilage and bone defect.

Referring to FIGS. 2A through 2D, the inner sleeve 12 includes a proximal end 18 and a distal end 20 opposite thereof, and an aperture 22 that extends from the proximal end 18 to the distal end 20. The inner sleeve 12 includes two distinguishable portions, namely, a cylindrical-shaped portion 24, which is positioned at the proximal end 18, and an elongated tubular member 26 that extends axially from the portion 24 to the distal end 20. The tubular member 26 tapers gradually toward the distal end 20. A circular-shaped rim 28 is formed where the portion 24 and the tubular member 26 meet.

Still referring to FIGS. 2A through 2D, the portion 24 has an exterior surface 30, which defines an outside diameter D1 of the portion 24, and an interior surface 32, which defines an inside diameter D2 of the portion 24. The tubular member 26 has an exterior surface 34, which defines an outside diameter D3 of the tubular member 26, and an interior surface 36, which defines an inside diameter D4 of the tubular member 26. It is noted that the outside diameter D1 of the portion 24 is greater than the outside diameter D3 of the tubular member 26, while their inside diameters D2 and D4, respectively, are generally equal to one another where the portion 24 and the tubular member 26 meet (i.e., at the rim 28). Because the tubular member 26 tapers along its length from the rim 28 to the distal end 20, the outside and inside diameters D3, D4 of the tubular member 26, and, consequently, the wall thickness of the tubular member 26 and the size of the aperture 22, gradually decrease towards the distal end 20. As a result, the portion 24 is substantially rigid, while the tubular member 26 is generally soft and flexible, especially at and near the distal end 20. The reason that the tubular member 26 includes this feature shall be described in greater detail hereinafter. Alternatively, the tubular member 26 need not be tapered (i.e., the outside and inside diameters D3 and D4 remain constant), and the associated wall thickness of the tubular member 26 can be thin enough so that the tubular member 26 is generally soft and flexible.

With continued reference to FIGS. 2A through 2D, a pair of diametrically opposed, elongated fins 38 extend outwardly from and longitudinally on the exterior surface 30 of the portion 24. While the portion 24 includes the two fins 38, it may include more or less than two. A plurality of spaced-apart, elongated ribs 40 extends outwardly from and longitudinally on the interior surface 32 of the portion 24. While the portion 24 includes the three ribs 40 as shown, it may include more or less than three. An alignment indicator 41 extends longitudinally on the exterior surface 30 of the portion 24 proximate to the rim 28. The purposes and functions of the fins 38, the indicator 41, and the ribs 40 shall be described hereinafter.

Figure 2D:
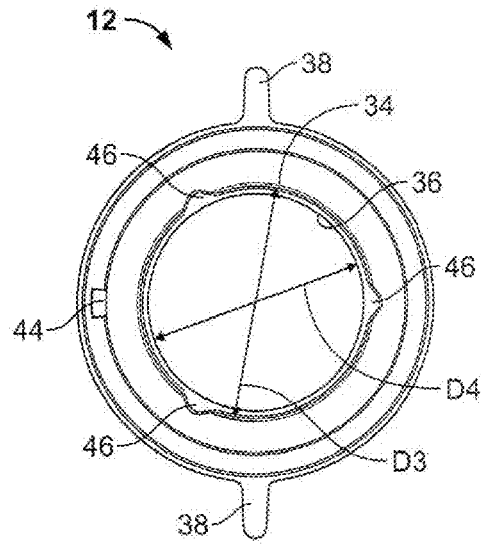
FIG. 2D is rear elevational view of a proximal end of the inner sleeve illustrated in FIG. 2A.
Figure 3A:
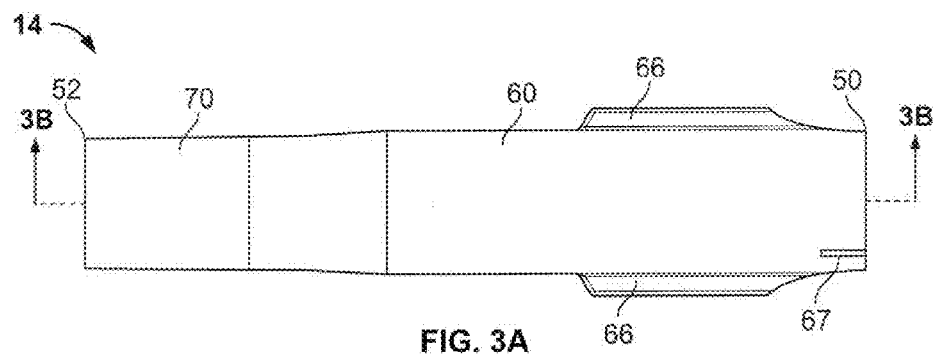
FIG. 3A is a side elevational view of an outer collar utilized by the implant inserter device illustrated in FIG. 1.
Figure 3B:
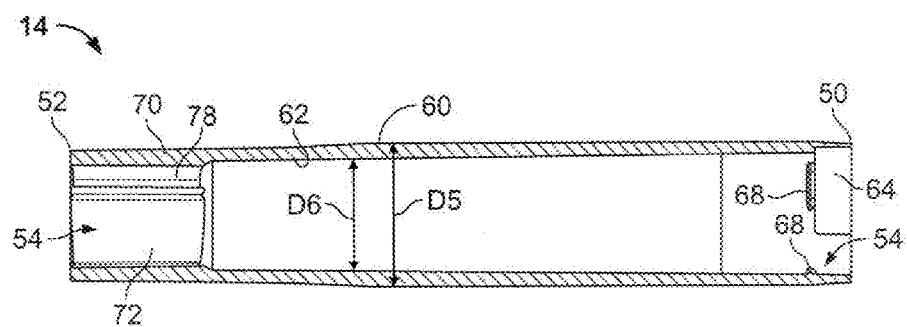
FIG. 3B is a cross-sectional view, taken along section line 3B-3B and looking in the direction of the arrows, of the outer collar illustrated in FIG. 3A.
Figure 3C:
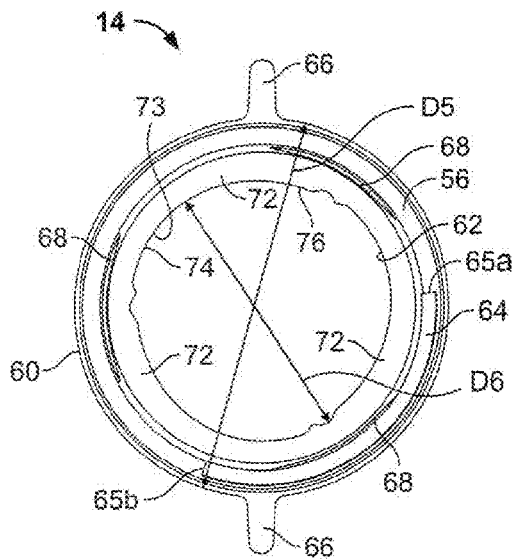
FIG. 3C is a front elevational view of a proximal end of the outer collar illustrated in FIG. 3A.
Figure 3D:
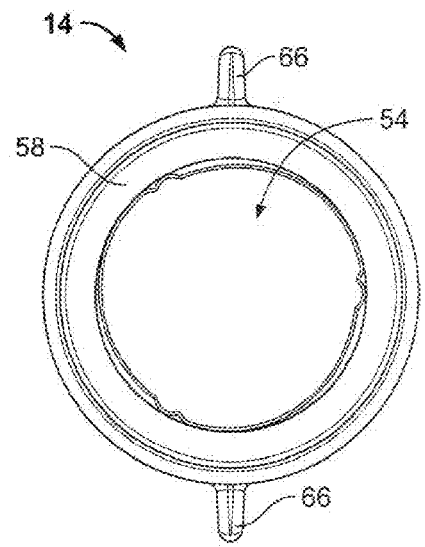
FIG. 3D is a rear elevational view of a distal end of the outer collar illustrated in FIG. 3A.

With continued reference to FIGS. 2A through 2D, a retaining groove 42 is formed circumferentially within the exterior surface 34 of the tubular member 26 proximate to the rim 28 (see, specifically, FIG. 2A), while a rectangular-shaped stop member 44 extends outwardly from and longitudinally on the exterior surface 34 of the tubular member 26 from the rim 28 to the retaining groove 42 (see, specifically, FIG. 2D). In addition, a plurality of spaced-apart, elongated ribs 46 extend outwardly from and longitudinally on the exterior surface 34 of the tubular member 26 from the distal end 20 to a point 48 intermediate the distal end 20 and the retaining groove 42 (see FIG. 2A). While the tubular member 26 includes three of the ribs 46, it may include more or less than three. The purposes and functions of the retaining groove 42, the stop member 44, and the ribs 46 shall be described hereinafter.

Referring to FIGS. 3A through 3D, the outer collar 14 includes a proximal end 50 and a distal end 52 opposite thereof, and an aperture 54 that extends from the proximal end 50 to the distal end 52. The proximal end 50 includes a circular-shaped rim 56, while the distal end 52 includes a circular-shaped rim 58. The outer collar 14 has an exterior surface 60, which defines an outside diameter D5 thereof, and an interior surface 62, which defines an inside diameter D6 thereof. A rectangular-shaped slot 64 is formed within the rim 56, extending from the interior surface 62 to a point approximately intermediate to the exterior surface 60. The length of the slot 64 is approximately one-quarter of the circumference of the rim 56, extending between end walls 65a, 65b. The purpose and function of the slot 64 will be described hereinafter.

Still referring to FIGS. 3A through 3D, a pair of diametrically opposed, elongated fins 66 extend outwardly from and longitudinally on the exterior surface 60 of the outer collar 14. While the outer collar 14 includes the two fins 66, it may include more or less than two. An alignment indicator 67 extends longitudinally on the exterior surface 60 proximate to the rim 56. A plurality of spaced-apart hooks 68 extends outwardly from and circumferentially on the interior surface 62 of the outer collar 14 proximate to the proximal end 50. While the outer collar 14 includes three of the hooks 68 as shown, it may include more or less than three. The purposes and functions of the fins 66, the indicator 67, and the hooks 68 shall be described hereinafter.

With continued reference to FIGS. 3A through 3D, the outer collar 14 includes a tapered portion 70 formed at the distal end 52. A plurality of ramps 72 are formed on the interior surface 62 of the tapered portion 70 and proximate to the distal end 52. Each of the ramps 72 has a curvilinear, ramp-like shaped surface 73 that inclines gradually from a lower portion 74 to an elevated portion 76 (see, specifically, FIG. 3C). Each of the ramps 72 is spaced apart from one another. Alternatively, the ramps 72 may be positioned adjacent to one another. While the outer collar 14 includes the three ramps 72, it may include more or less than three. The purpose and function of the ramps 72 shall be described hereinbelow.

Figure 4A:
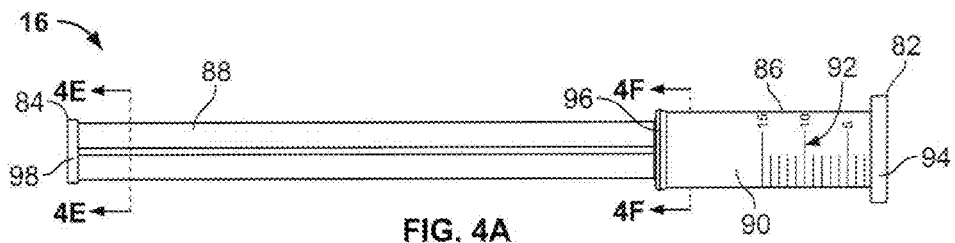
FIG. 4A is a top elevational view of a push rod utilized by the implant inserter device illustrated in FIG. 1.
Figure 4B:
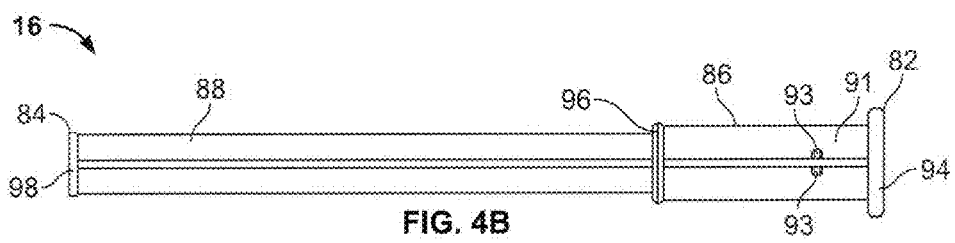
FIG. 4B is a bottom elevational view of the push rod illustrated in FIG. 4A.
Figure 4C:
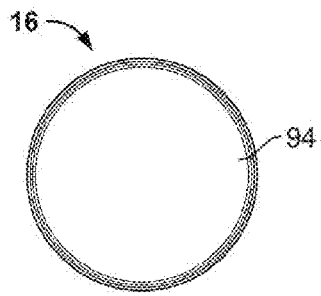
FIG. 4C is a rear elevational view of a proximal end of the push rod illustrated in FIG. 4A.
Figure 4D:
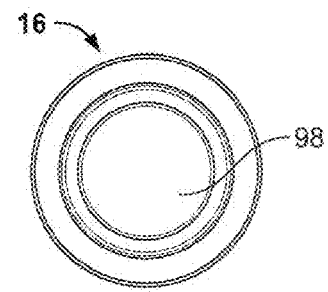
FIG. 4D is a front elevational view of a distal end of the push rod illustrated in FIG. 4A.
Figure 4E:
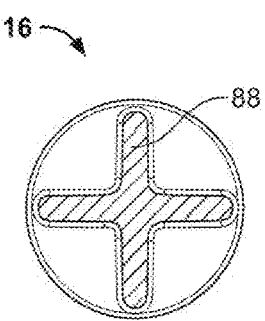
FIG. 4E is a cross-sectional view, taken along section line 4E-4E and looking in the direction of the arrows, of the push rod illustrated in FIG. 4A.
Figure 4F:
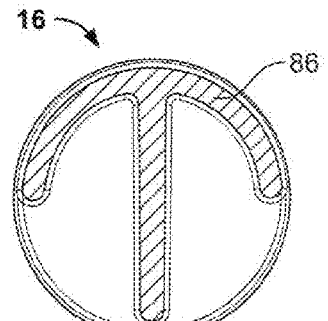
FIG. 4F is a cross-sectional view, taken along section line 4F-4F and looking in the direction of the arrows, of the push rod illustrated in FIG. 4A.

Referring to FIGS. 4A through 4E, the push rod 16 has a proximal end 82 and a distal end 84 opposite thereof, a calibration portion 86 having a generally T-shaped cross section (see FIG. 4F) and positioned at the proximal end 82, and an elongated shaft 88 having a cross-shaped cross section and which extends longitudinally from the calibration portion 86 to the distal end 84. The calibration portion 86 includes an exterior surface 90 having indicia 92 printed thereon, such as, for example, an implant length scale depicting measurement in millimeters. An interior surface 91 of the calibration portion 86 includes a set of locking tabs 93, whose function shall be described hereinafter. A disc-shaped head 94 is positioned at one end of the calibration portion 86, while a friction ring 96 is positioned at the other end of the calibration portion 86. A disc-shaped base 98 is positioned at the distal end 84. The purposes and functions of the head 94, friction ring 96 and the base 98 shall be discussed hereinafter. While the push rod 16 is, preferably, constructed as shown in FIGS. 4A through 4E, it can consist of other appropriate shapes and sizes and of other push rods or plungers known in the art. For example, the calibration portion 86 and/or the shaft 88 may each have a cross-section consisting of different shapes and sizes, such as circular, hexagonal, etc.

The inner sleeve 12 is, preferably, manufactured from a translucent polymer material, such as polypropylene, while the outer collar 14 and the push rod 16 are, preferably, manufactured from an opaque polymer material, such as polycarbonate. Alternatively, the outer collar 14 and the push rod 16 may be made from other materials known in the art, such as stainless steel. Moreover, the inner sleeve 12, the outer collar 14, and the push rod 16 may each be transparent, translucent, or opaque, and each can be colored.

Figure 5D:
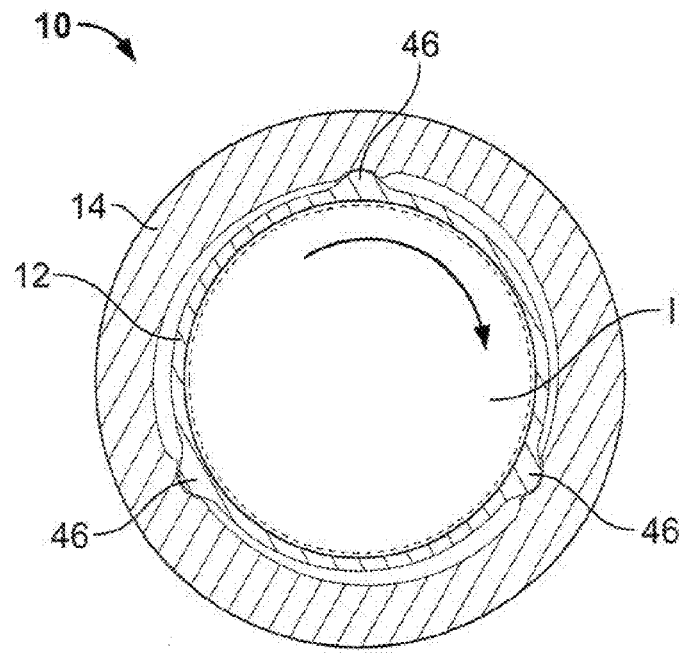
FIG. 5D is a cross-sectional view, taken along section line 5D-5D and looking in the direction of the arrows, of the implant inserter device illustrated in FIG. 5A, with the device being shown in an unlocked position and disengaged with an implant that is shown in phantom.

FIGS. 5A through 5C show the implant inserter device 10 as fully assembled and the implant I housed therein. More particularly, the distal end 20 of the inner sleeve 12 is inserted into the aperture 54 of the outer collar 14 (the aperture 54 being shown in FIG. 3D) at the proximal end 50 thereof. During this stage of the assembly process, it is noted that the stop member 44 of the inner sleeve 12 (the stop member 44 being shown in FIG. 2D) must align with and be received within the slot 64 of the outer collar 14 (the slot 64 being shown in FIG. 3C), otherwise the stop member 44 will be impeded by the rim 56 of the outer collar 14 and full insertion of the inner sleeve 12 within the outer collar 14 will be prevented (not shown in the Figures). When the inner sleeve 12 is fully inserted within the outer collar 14, the rim 28 of the inner sleeve 12 abuts the proximal end 50 of the outer collar 14, resulting in the portion 24 of the inner sleeve 12 being fully exposed from, and the tubular member 26 being sheathed by, the outer collar 14. In such fashion, the distal end 20 of the inner sleeve 12 and the distal end 52 of the outer collar 14 are aligned with one another, as illustrated in FIG. 5B. Moreover, as shown in FIG. 5C, each of the hooks 68 of the outer collar 14 engage (e.g., snap into) the retaining groove 42 of the inner sleeve 12, resulting in the inner sleeve 12 and outer collar 14 being removably interlocked with one another.

It is further noted that the hooks 68 and the retaining groove 42 are sized and shaped to allow for the rotation of the outer collar 14 relative to the inner sleeve 12, and vice versa. As indicated above, the stop member 44 of the inner sleeve 12 is received within the slot 64. The end walls 65a, 65b of the slot 64 limit the rotation of the outer collar 14 relative to the inner sleeve 12 to approximately ninety degrees, i.e., about a one-quarter turn (not shown in the Figures).

When the stop member 44 abuts the end wall 65a, the distal end 20 of the inner sleeve 12 is in a "non-deformed" state and the implant inserter device 10 is considered to be in its "unlocked" position. The fins 38 of the inner sleeve 12 and the fins 66 of the outer collar 14 allow for a user to grip them to facilitate the rotation of the inner sleeve 12 relative to the outer collar 14. The fins 38 and the fins 66 also provide a visual indication that the device 10 is in its "unlocked position," such that one of the fins 38 align with a corresponding one of the fins 66 (see FIG. 5A). Moreover, the indicators 41, 67 align with one another when the implant inserter device 10 is in its unlocked position (see specifically FIG. 5A). While the implant inserter device 10 includes the fins 38 and the fins 66, the device 10 may include other means for gripping the inner sleeve 12 and the outer collar 14 in order to facilitate their rotation relative to one another. For instance, the exterior surface 30 of the inner sleeve 12 and/or the exterior surface 60 of the outer collar 14 may include ribs, knurling, raised beads or other roughening features to enhance gripping (not shown in the Figures). The exterior surface 30 of the inner sleeve 12 and/or the exterior surface 60 of the outer collar 14 may also include a soft overmolding or covering, such as plastic or rubber, to provide a gripping surface (not shown in the Figures).

When the implant inserter device 10 is in its "unlocked" position, the implant I is inserted within the aperture 22 of the inner sleeve 12 at the proximal end 18 thereof. The implant I is permitted to travel through the portion 24 and into the tubular member 26. Preferably, the distal end 20 of the inner sleeve 12 is sized and shaped such that no portion of the implant I is permitted to exit the distal end 20 without manual intervention by a user. Once the implant I is inserted into the inner sleeve 12, the distal end 84 of the push rod 16 is inserted into the aperture 22 of the inner sleeve 12 at the proximal end 18 thereof, until the base 98 of the push rod 16 engages the implant I. A user may depress the push rod 16 to further position the implant I within the tubular member 26 of the inner sleeve 14, should it be necessary. The ribs 40 of the inner sleeve 12 frictionally engage the calibration portion 86 of the push rod 16.

Once the implant I is positioned within the inner sleeve 14 as desired, it may then be "locked" into position. More particularly, the inner sleeve 12 is rotated clockwise approximately ninety degrees relative to the outer collar 14, until the stop member 44 abuts the end wall 65b. Once again, the fins 38 of the inner sleeve 12 and the fins 66 of the outer collar 14 allow for a user to grip them to facilitate the rotation of the inner sleeve 12 and the outer collar 14. In addition, the fins 38 and the fins 66 provide a visual indication that the device 10 is in its "locked" position, such that the fins 38 are positioned perpendicular to the fins 66. Also, when the device 10 is in an unlocked position, the indicators 41, 67 no longer align, thus providing another visual indication. The inner sleeve 12 and the outer collar 14 may include indicia printed thereon (such as "lock" and "unlock" symbols and a position line) that indicates the implant inserter device's 10 locked and unlocked positions (not shown in the Figures).

Figure 5E:
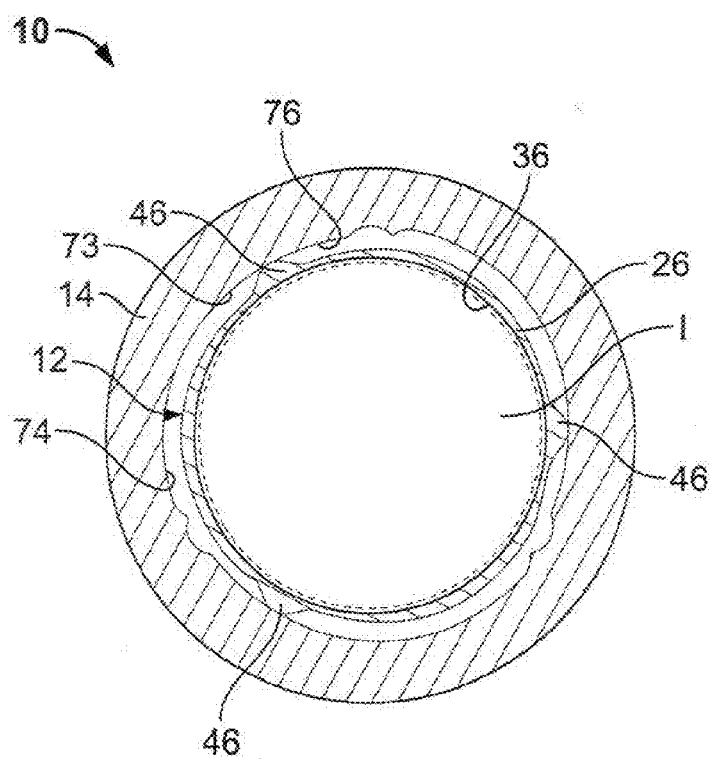
FIG. 5E is the same cross-sectional view of the implant inserter device shown in FIG. 5D, but with the device being shown in a locked position and engaged with the implant.

As the inner sleeve 12 is rotated relative to the outer collar 14, each of the ribs 46 of the inner sleeve 12 travel along the surface 73 of a corresponding one of the adjacent ramps 72 from the declined portion 74 to the inclined portion 76 (see FIG. 5E). In view of the fact that the distal end 20 of the inner sleeve 14 is soft and flexible, and thus, deformable, the inner diameter D4 of the tubular member 26 proximate to the distal end 20 decreases (i.e., collapses) as the ribs 46 travel along the surfaces 73 of the ramps 72. Consequently, the interior surface 36 of the tubular member 26 grips the implant I. Thus, when the device 10 is in its locked position, the implant I is secured by the inner sleeve 12.

The implant I may be preloaded within the implant inserter device 10 and packaged and stored as a unit before actual use thereof during a surgical procedure. In this case, it is preferred that the implant inserter device 10 be set in its "locked" position prior to loading the implant I therein. In this regard, the distal end 20 of the inner sleeve 12 will be deformed and have a diameter that is less than the diameter of the implant I; and, therefore, the implant I remains positioned in an area before the distal end 20 of the inner sleeve 12. If the implant inserter device 10 is not locked prior to loading the implant I, the implant I could continue to travel through the inner sleeve 12 and the distal end of the implant I would be at or proximate to the distal end 20 of the inner sleeve 12. Another reason that the implant inserter device 10 should be set in its locked position during storage is to set the distal end 20 of the inner sleeve 12 in a deformed manner. While the inner sleeve 12 is sized to prevent the implant I from prematurely exiting when the implant inserter device 10 is in its unlocked position, the implant I could vary slightly in diameter and there is a chance that it could start to slide out of the distal end 20 of the inner sleeve 12 during a surgical procedure. Thus, the deformation of the inner sleeve 12 prevents this from happening.

Although the implant I is preferably preloaded as described above, the implant I need not be preloaded, and a user may load the implant I within the implant inserter device 10 during the actual surgical procedure. In addition, several sizes and shapes of the implant inserter device 10 can be stocked at a surgery site, as needed, such as 8 mm, 10 mm, 12 mm, 15 mm, 18 mm, and 20 mm.

Referring to FIGS. 6A through 6D, a miter cap 100 includes a rectangular-shaped cap portion 102 having a first surface 104 and a second surface 106 opposite thereof, and a rectangular-shaped base 108 extending outwardly and perpendicular from the cap portion 102 at a lower end 110 thereof. A tubular shaft 112 extends outwardly from the second surface 106 of the cap portion 102, and includes a circular-shaped aperture 114 extending therethrough (see, in particular, FIGS. 6C and 6D). A plurality of crush ribs 115 extend longitudinally from the interior surface of the shaft 112. A pair of parallel, spaced-apart legs 116a, 116b extends from the shaft 112. A circular-shaped aperture 118 extends from the first surface 104 to the second surface 106 of the cap portion 102 and is positioned concentrically with the aperture 114 of the shaft 112. The miter cap 100 is, preferably, made from a polymer plastic material, but it may be made from other suitable materials known in the art. The function and purpose of the miter cap 100 shall be discussed hereinbelow.

Figure 6A:
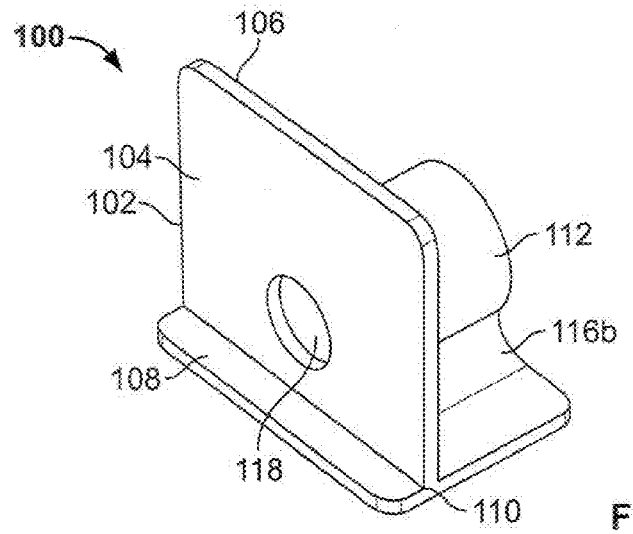
FIG. 6A is a front perspective view of a miter cap utilized in connection with the implant inserter device illustrated in FIG. 1.
Figure 6B:
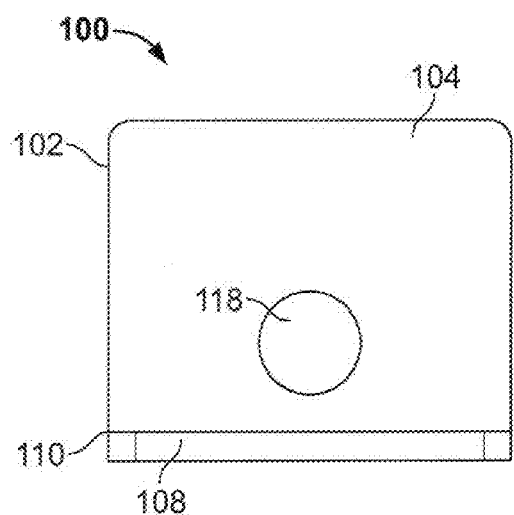
FIG. 6B is front elevational view of the miter cap illustrated in FIG. 6A.
Figure 6C:
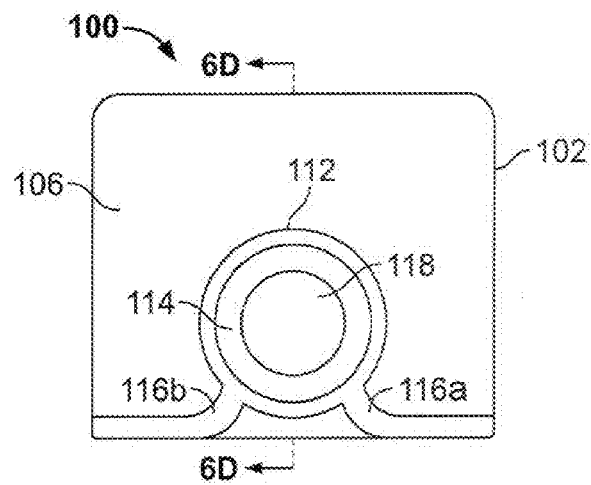
FIG. 6C is rear elevational view of the miter cap illustrated in FIG. 6A.
Figure 6D:
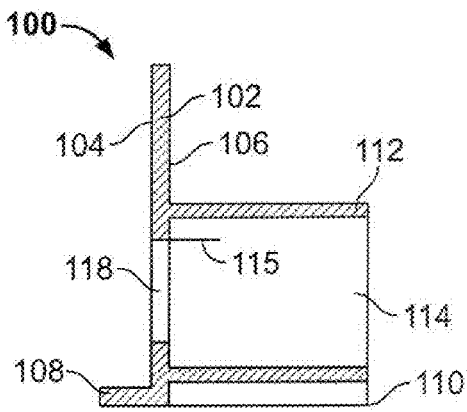
FIG. 6D is a cross-sectional view, taken along section line 6D-6D and looking in the direction of the arrows, of the miter cap illustrated in FIG. 6C.
Figure 6E:
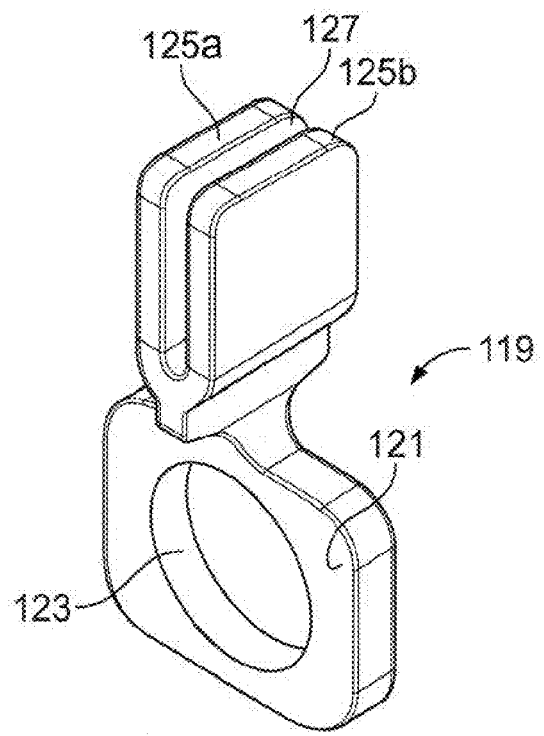
FIG. 6E is a front perspective view of a stop utilized in connection with the implant inserter device illustrated in FIG. 1.
Figure 6F:
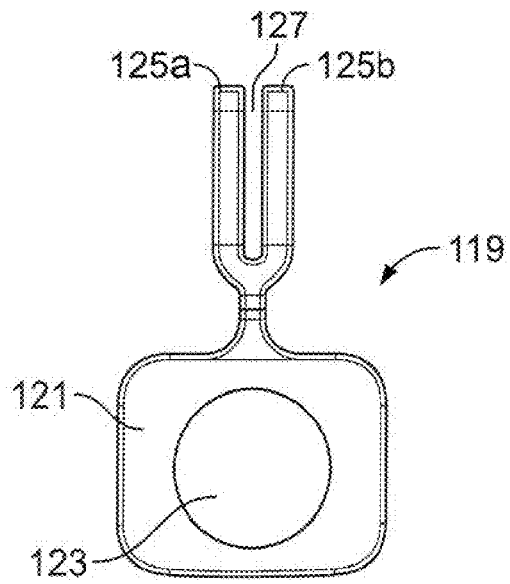
FIG. 6F is a front elevational view of the stop shown in FIG. 6E.

Referring to FIGS. 6E and 6F, a stop member 119 includes a rectangular-shaped pull tab 121 having a circular shaped aperture 123, and a pair of arms 125a, 125b that extend outwardly from the pull tab 121 and parallel to one another. The arms 125a, 125b form a space 127 therebetween. Alternatively, the pull tab 121 need not include the aperture 123 and, instead, include other gripping means known in the art, such as elongated ribs, an array of detents, etc. (not shown in FIGS. 6E and 6F). The stop member 119 is, preferably, made from a polymer plastic material, but it may be made from other suitable materials known in the art. The function and purpose of the stop member 119 shall be discussed hereinbelow.

Figure 6G:
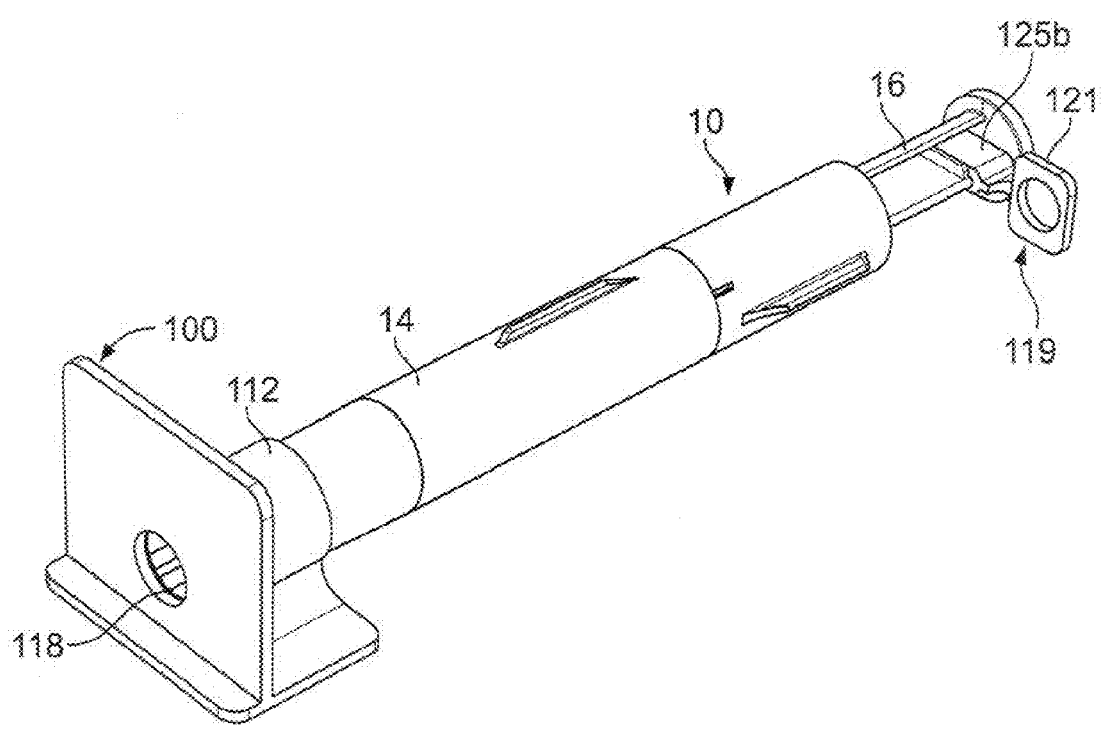
FIG. 6G is a front perspective view of the implant inserter device shown in FIG. 1 in its locked position, the miter cap shown in FIG. 6A, and the stop shown in FIG. 6E assembled with one another.

Referring to FIG. 6G, the implant inserter device 10 is coupled with the miter cap 100, such that the distal end 52 of the outer collar 14 of the device 10 is inserted into the aperture 114 of the shaft 112. The aperture 114 is sized and shaped such that the distal end 52 of the outer collar 14 is secured frictionally and removably therein. The crush ribs 115 of the shaft 112 also provide further security (not shown in FIG. 6G). As will be described in greater detail below, the diameter of the aperture 54 of the outer collar 14 at the distal end 52 is generally equal to the diameter of the aperture 118 of the miter cap 100, which would, therefore, allow for the implant I to travel through the aperture 118.

Figure 7A:
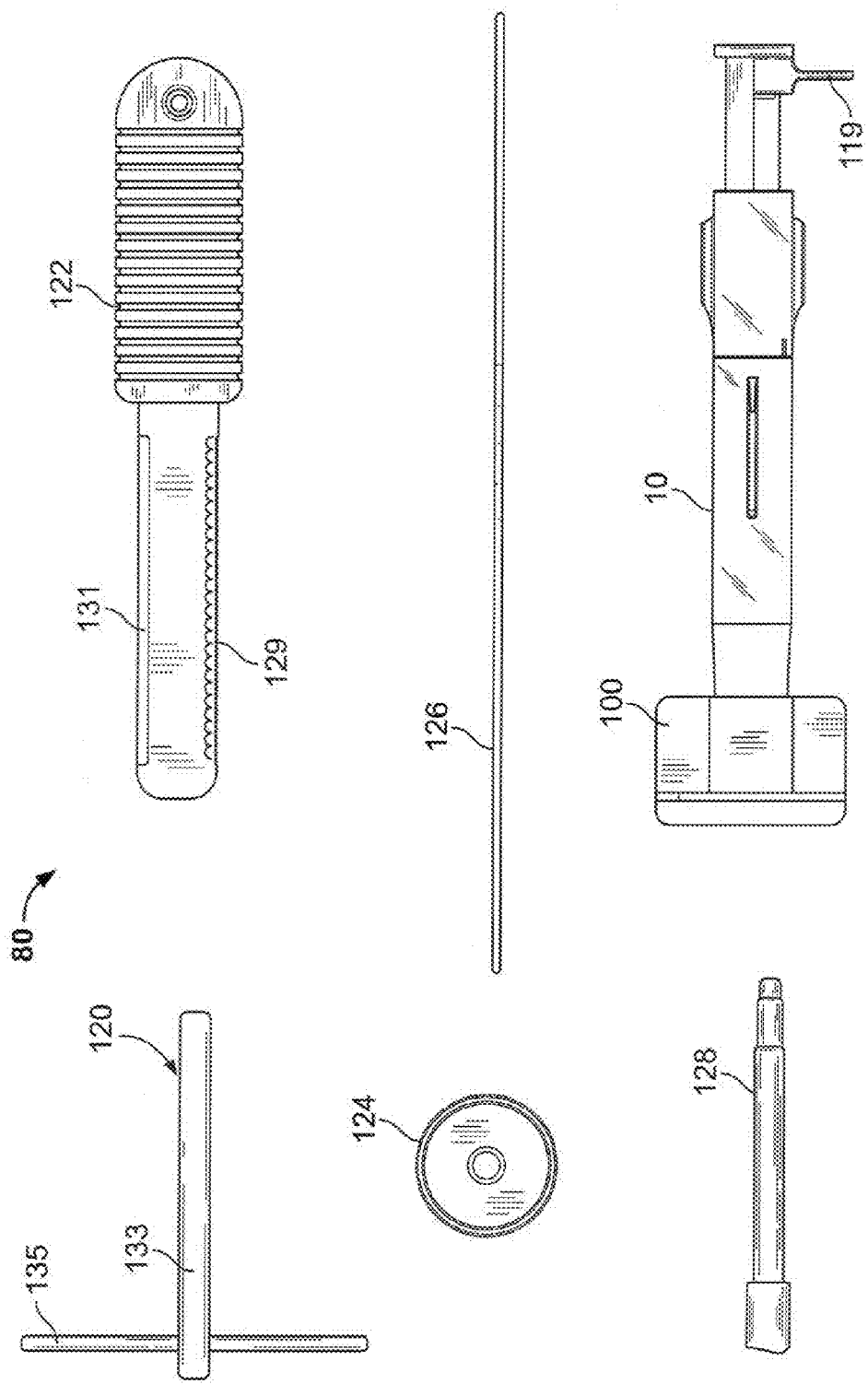
FIG. 7A illustrates a set of disposable surgical instruments used for repairing cartilage and bone damage, including the implant inserter device assembly shown in FIG. 6G.
Figure 7B:
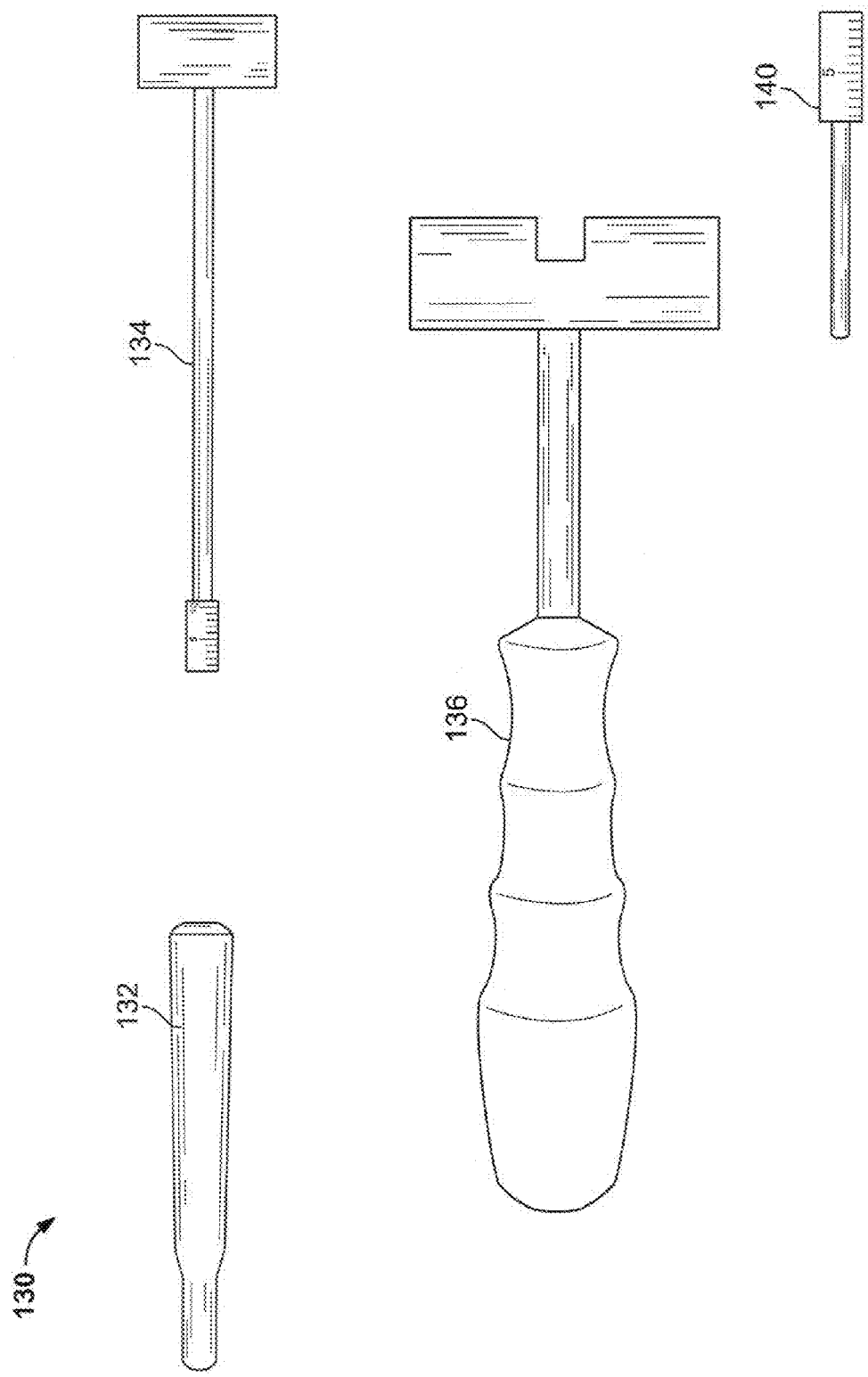
FIG. 7B illustrates a set of reusable surgical instruments used for repairing cartilage and bone damage, which are used in conjunction with the disposable surgical instruments shown in FIG. 7A.

With continued reference to FIG. 6G, the stop member 119 is clipped onto the push rod 16, such that the arms 125a, 125b engage the interior surface 91 of the calibration portion 86, which is received within the space 127. The locking tabs 93 prevent the stop member 119 from sliding axially on the push rod 16. As described in more detail below, the stop member 119 acts as a mechanical cue to a user to remind her not to cut the implant I too short. FIGS. 7A and 7B show two sets of surgical instruments for repairing damage to cartilage and bone. With particular reference to FIG. 7A, a disposable kit 80 includes the implant inserter device 10 with the miter cap 100 and the stop member 119 coupled thereto, a scoring tool 120, a surgical knife 122, a disc-shaped chamfering tool 124, a guide wire 126, and a lesion reamer 128. It is noted that the knife 122 includes a cutting edge 129 and a chamfering edge 131 opposite thereof. The chamfering sections on the knife 122 and the chamfering tool 124 are made using a process disclosed in U.S. Pat. No. 6,599,322. The scoring tool 120 includes a tubular-shaped scoring member 133 and a rod-shaped handle 135 attached to the scoring member 133 and extending therethrough perpendicularly for turning the scoring member 133. Alternatively, the scoring tool 120 need not include the handle 135 and the scoring member 133 can be turned by other means known in the art. The guide wire 126 and the lesion reamer 128 may consist of those found within Musculoskeletal Transplant Foundation's ACT™ surgical kit, but they may be made and supplied by other manufacturers.

As indicated above, the implant inserter device 10 may be preloaded with the implant I, but it need not be. While each of the aforesaid components of the disposable kit 80 are intended to be disposed of after use, they need not be and can be made to be reusable (e.g., for example, the chamfering tool 124). Moreover, while the disposable kit 80 includes the foregoing components, it can include less or additional components and/or include components that are equivalent to each.

With reference to FIG. 7B, the reusable kit 130 includes a lesion gauge 132, a dilator 134, a mallet 136, and a depth gauge 140, all of which may be found within Musculoskeletal Transplant Foundation's ACT™ surgical kit. Alternatively, these components may be made and supplied by other manufacturers. While each of these components are intended to be reusable, they need not be and can be made to be disposable. Moreover, while the reusable kit 130 includes the foregoing components, it can include less or additional components and/or include components that are equivalent to each. Furthermore, the components of the kits 80, 130 can be provided separately as described above, or they can be combined into a single kit.

Figure 8A:
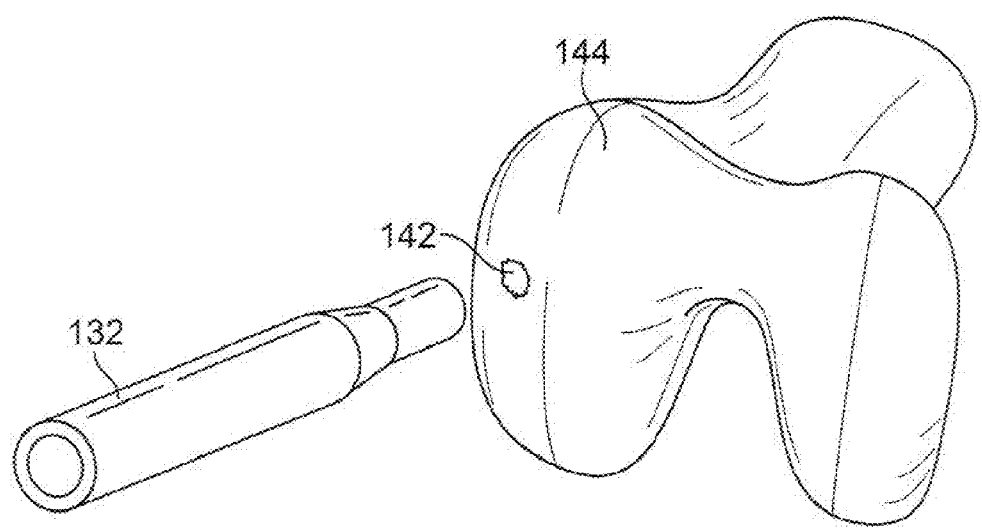
FIG. 8A is an exploded perspective view of a distal femur having an articular surface with a lesion defect thereon, and a lesion gauge illustrated in FIG. 7B.
Figure 8B:
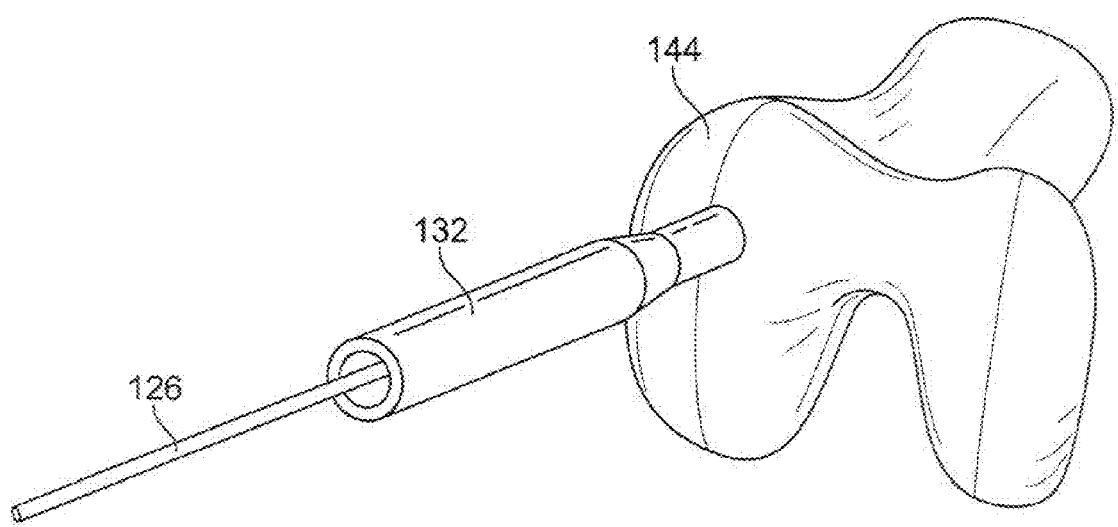
FIG. 8B is a perspective view of the femur and the lesion gauge shown in FIG. 8A, with the lesion gauge being positioned proximate to the defect and mounted on a guide wire shown in FIG. 7A.

FIGS. 8A through 8K show the steps of surgically repairing a lesion defect 142 in a distal femur 144 having an articular surface using the surgical instruments of the kits 80, 130. Typically, the defect 142 is arthroscopically located by an endoscope or similar device (not shown in the Figures). Once the defect 142 is located, the surgical site prepared for surgery (either for open surgery or arthroscopic surgery). With reference to FIG. 8A, the defect 142 is visualized and its approximate size are determined using the lesion gauge 132. The surgeon selects the lesion gauge 132 having a size that is closest to the size of the defect 142 so that the selected size is greater than or equal to the size of the defect 142. The lesion gauge 132 may be color coded to easily identify different sizes of defects. With reference to FIG. 8B, once the defect 142 is sized and measured, the guide wire 126 is aligned and inserted within the defect 142 using handheld drill or the like (not shown in the Figures). Preferably, the guide wire 126 is positioned perpendicular to the defect 142 as best as possible. After the guide wire 126 is positioned, the lesion gauge 132 is mounted on the guide wire 126 and the defect 142 is further measured.

Figure 8C:
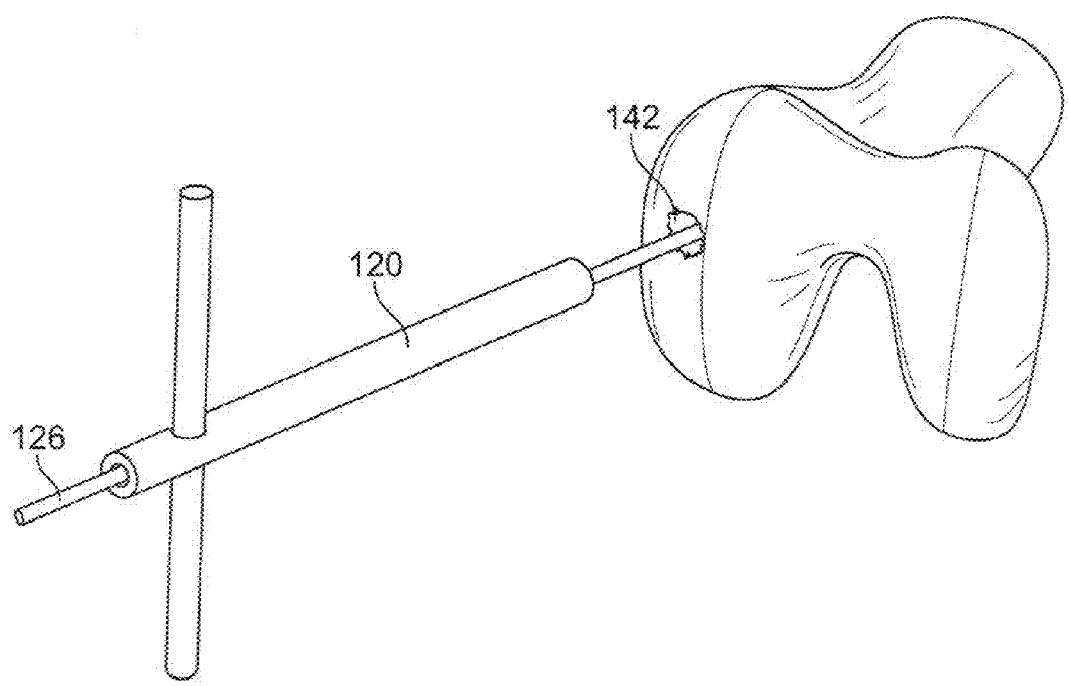
FIG. 8C is a perspective view of the femur and the guide wire shown in FIG. 8B and a scoring tool shown in FIG. 7A being mounted on the guide wire.
Figure 8D:
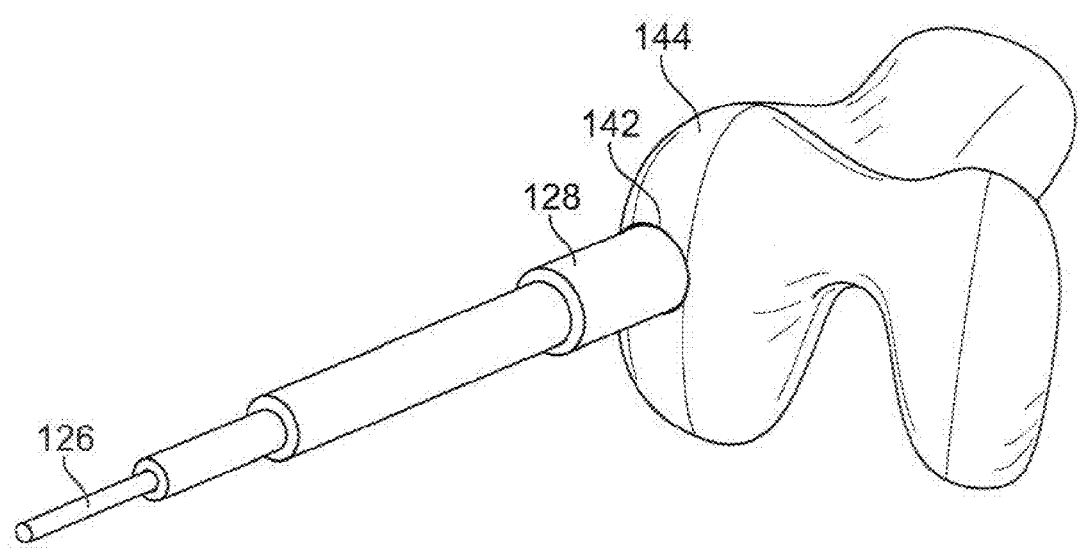
FIG. 8D is a perspective view of the femur and the guide wire shown in FIG. 8C, with a lesion reamer shown in FIG. 7A mounted on the guide wire.
Figure 8E:
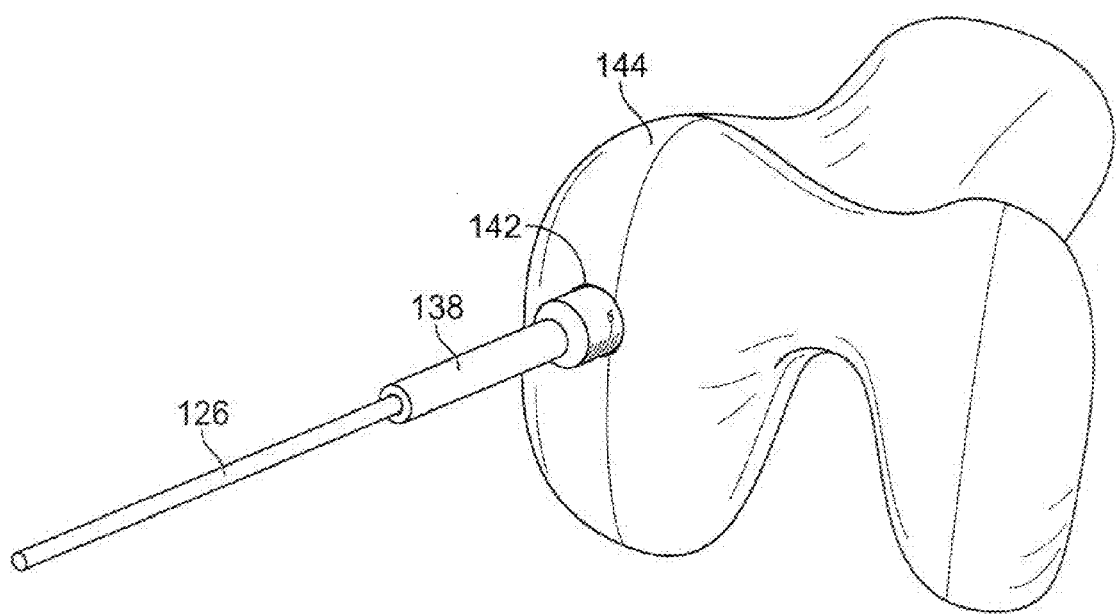
FIG. 8E is a perspective view of the femur and the guide wire shown in FIG. 8D, with a depth gauge shown in FIG. 7B mounted on the guide wire and positioned within a bored out defect site.

With reference to FIG. 8C, the lesion gauge 132 is removed and the scoring tool 120 is mounted on the guide wire 126. The scoring tool 120 is twisted a few times to break the fibrous cartilage lining the articular surface and provide a small pilot, circumferential cut (not shown in the Figures). In this regarding, using the lesion reamer 128 without first using the scoring tool 120 in the foregoing manner would tear up the cartilage lining, thus possibly creating further damage to the cartilage lining. With reference to FIG. 8D, the defect 142 is bored out using the lesion reamer 128 which is mounted on the guide wire 126. Alternatively, the lesion reamer 128 could be designed to perform both a scoring and a reaming operation; and, therefore, eliminate the need for the scoring tool 120. Next, as shown in FIG. 8E, the depth of the bored out defect 142 may be measured by using the depth gauge 140 mounted to the guide wire 126. Further boring may be necessary as determined by the surgeon. It is noted that the depth of the bored out defect 142 must not be greater than the maximum length of the implant I, nor can it be less than the design limits of a multi-component implant (not shown in the Figures). Once the appropriate depth of the bored out defect 142 has been achieved, the implant I is ready to be prepared.

Figure 8F:
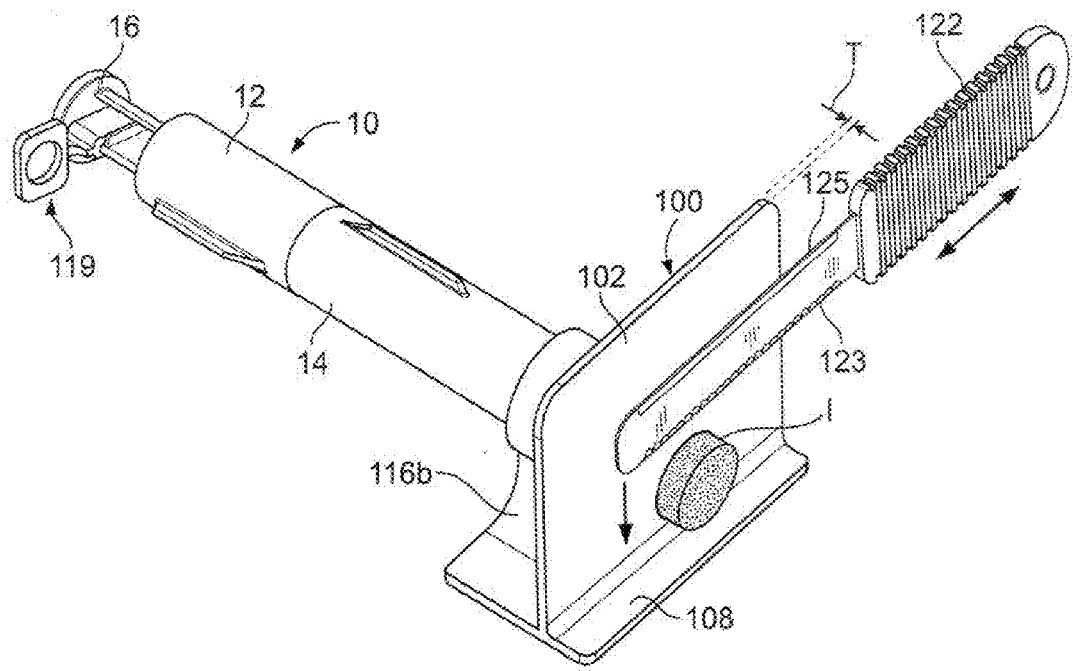
FIG. 8F is a front perspective review of the implant inserter device assembly and the surgical knife shown in FIG. 7A, with the knife being shown in a cutting position to cut an implant retained by the implant inserter device assembly.

Referring to FIG. 8F, the implant inserter device 10 is unlocked (i.e., by turning the inner sleeve 12 relative to the outer collar 14), which enables the implant I to be movable within the inner sleeve I. In this regard, the user depresses the push rod 16, which urges the implant I through the tubular member 26. When the push rod 16 is depressed, the friction ring 96 of the push rod 16 engages frictionally the interior surface 32 of the portion 24 in order to provide enhanced control of the push rod 16.

The implant exits the aperture 22 at the distal end 20 and, in turn, a portion of the implant I is exposed from the aperture 118 of the miter cap 100, until the desired depth is achieved. The desired depth is measured by reading the indicia 92 on the push rod 16 with respect to the proximal end 18 of the inner sleeve 12. It is noted that the wall thickness T of the cap portion 102 of the miter cap 100 is automatically taken into account when setting the desired length of implant I with the indicia 92 on the calibration portion 86 of the push rod 16. In other words, a user need only rely on the indicia 92 when setting the implant's I length.

As shown in FIG. 8F, once the desired length of the implant I is set, the implant I is locked into position by locking the implant inserter device 10 (i.e., by turning the inner sleeve 12 relative to the outer collar 14). The implant I may then be cut with the cutting edge 123 of the surgical knife 122 to the desired length. The miter cap 100 serves as a cutting guide. The base 108 of the miter cap 100 protects the surface where it lies upon, as well as any surgical drapes, while the legs 116a, 116b provide stability.

As indicated above, the stop member 119 acts as a mechanical cue to a user to remind her not to cut the implant I too short. For example, the stop member 119 can be positioned on the push rod 16 to prevent it from traveling too far and the implant I from being exposed too much to be cut, for instance, below 9 mm. This assures that the length of the implant I is maintained at a minimum length (e.g., 9 mm) and prevents a surgeon from inadvertently cutting it down too much.

Figure 8G:
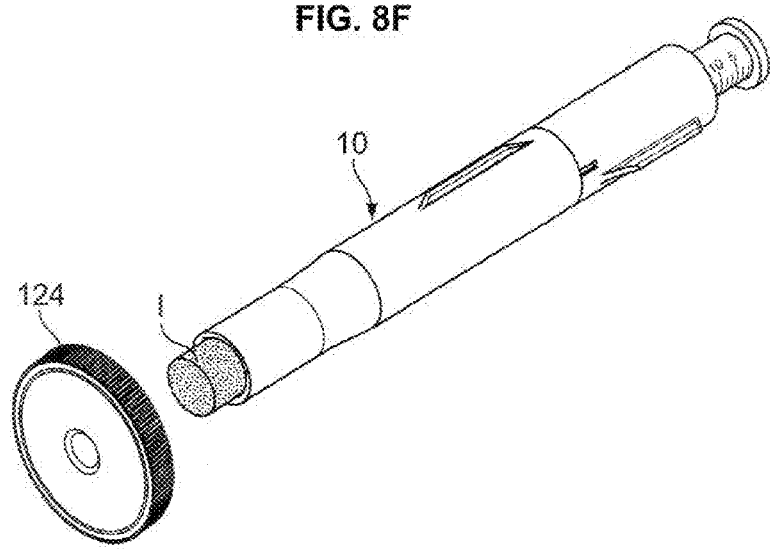
FIG. 8G is an exploded front perspective view of the implant inserter device shown in FIG. 8F, but with the miter cap removed, and a chamfering device shown in FIG. 7A.

Referring to FIG. 8G, once the implant I is trimmed to its desired length, the miter cap 100 and the stop member 119 are removed and the chamfering tool 124 is used to create a chamfer on the leading edge of the implant I. The chamfered edge of the implant I is created so that the implant I finds the bored out defect 142 during the insertion process. Alternatively, the chamfering edge 125 of the surgical knife 122 may be used to create a chamfering edge on the implant I.

Figure 8H:
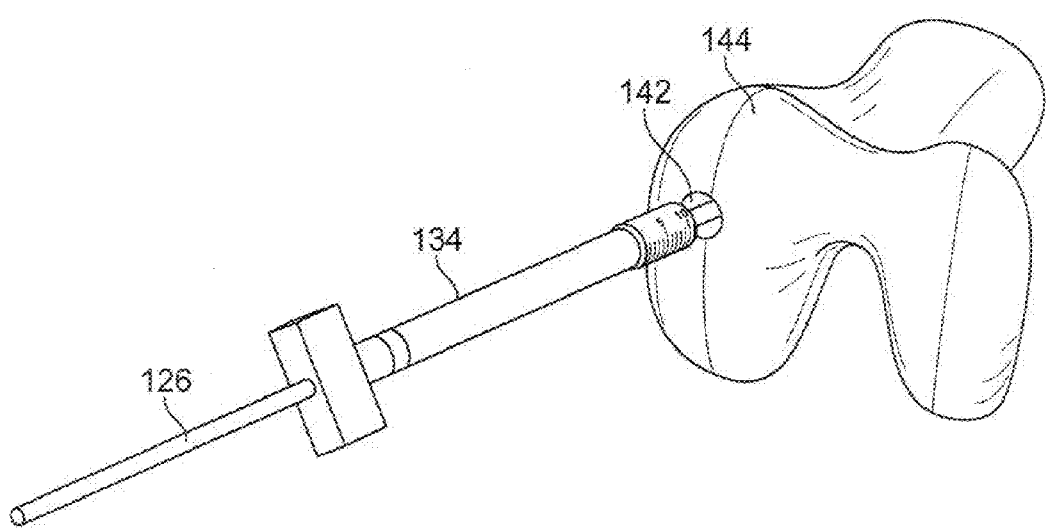
FIG. 8H is a front perspective view of the femur and the guide wire shown in FIG. 8E, with a dilator shown in FIG. 7B mounted on the guide wire and positioned proximate to the bored out defect site.
Figure 8I:
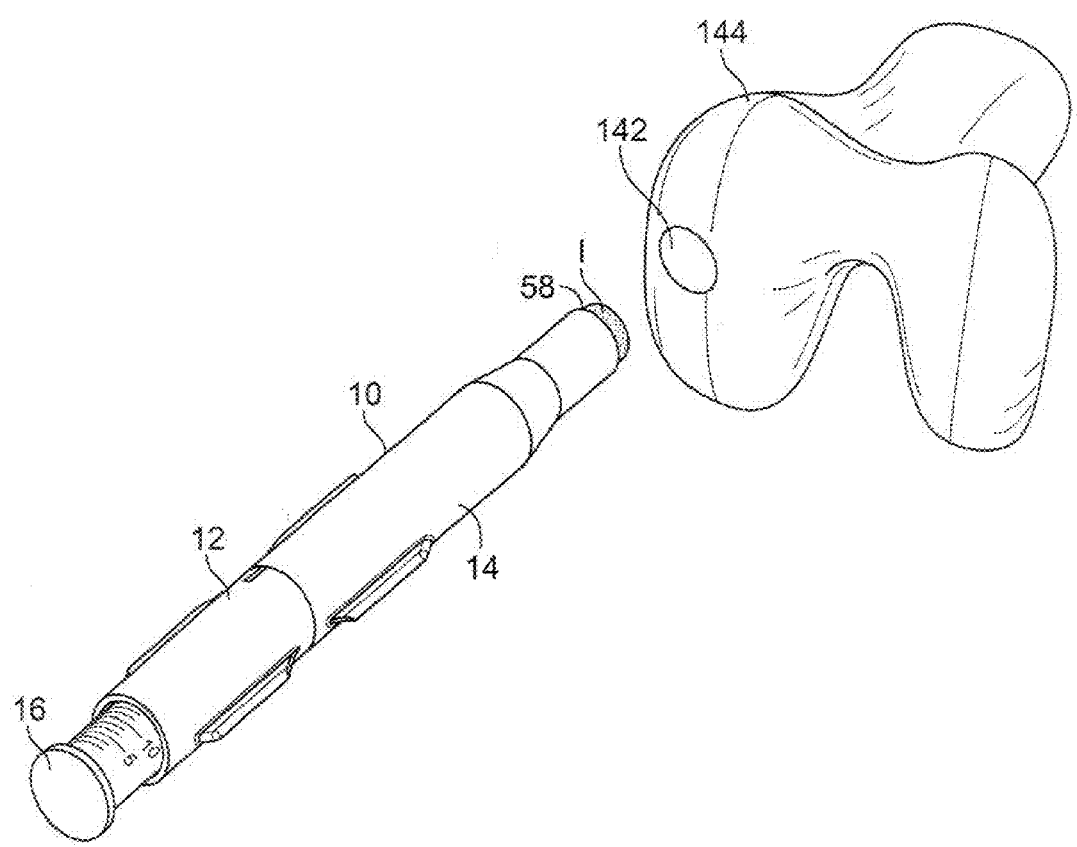
FIG. 8I is an exploded perspective view of the femur shown in FIG. 8H and the implant inserter device shown in FIG. 8G positioned away from the bored out defect site prior to implantation.

Referring to FIG. 8H, the dilator 134 is mounted on the guide wire 126 and the site of the defect 142 is dilated using the mallet 136. Once the defect 142 has been dilated appropriately, the dilator 134 and the guide wire 126 are removed. Referring to FIG. 8I, the implant I is ready for insertion into the defect 142. To this end, the surgeon positions the implant inserter device 10 so that the chamfered edge of the implant I finds and aligns with the defect 142. Once the implant I is properly positioned, the surgeon unlocks the implant inserter device 10 by turning the inner sleeve 12 relative to the outer collar 14, and fully depresses the push rod 16, either by hand or with the mallet 136. The base 98 of the push rod maintains a uniform normal force on the implant I.

Figure 8J:
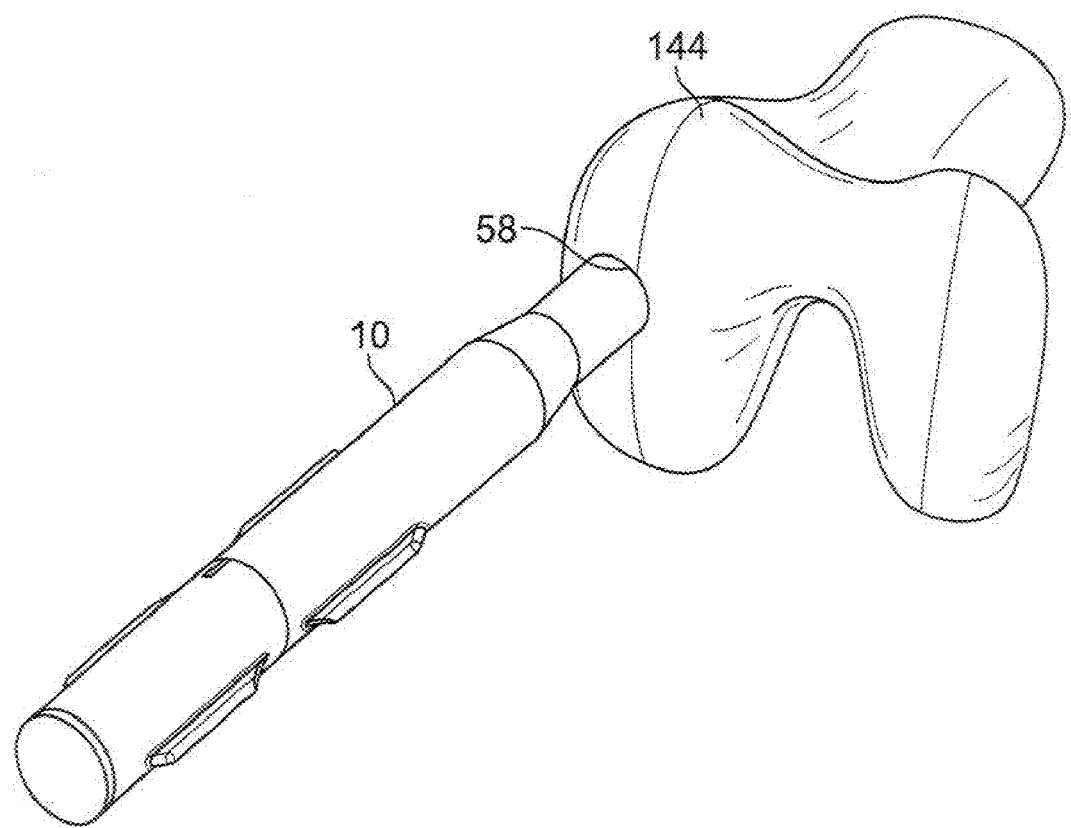
FIG. 8J is a front perspective view of the femur and the implant inserter device shown in FIG. 8I, with the implant inserter device positioned proximate to the bored out defect site.

During the insertion procedure, the rim 58 of the outer collar 14 is kept flush with the articular surface, as shown in FIG. 8J. Because the inner sleeve 12 and the outer collar 14 may be made from a transparent or a translucent material, the surgeon is able to visualize the position of implant I throughout surgical procedure, including during the implant cutting process and the insertion process.

It also noted that no portion of implant inserter device 10 is inserted within the defect 142. Furthermore, when the push rod 16 is fully depressed, the head 94 of the push rod 16 abuts against the rim 56 of the outer collar 14, and, thus, preventing the push rod 16 from pushing the implant I below flush with respect to the defect 142.

Figure 8K:
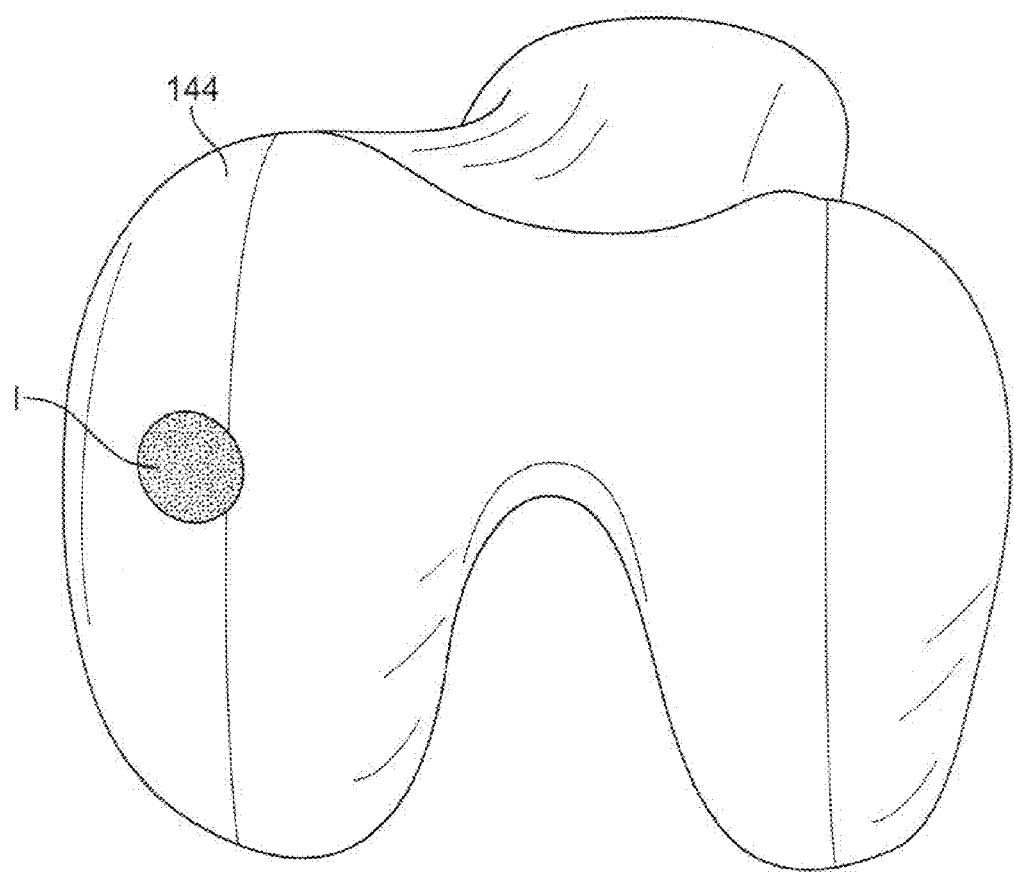
FIG. 8K is a perspective view of the femur shown in FIG. 8J with the implant inserted into the bored out defect site.

At this point, it is desirable not to have the implant I proud or recessed in relation to the defect 142, especially with large size implants or on curved surfaces. The implant I is set flush using the mallet 136. Once the implant I is flush, as shown in FIG. 8K, it is hydrated and the surgical site is cleaned and closed.

It will be understood that the embodiment described herein is merely exemplary and that a person skilled in the art may make many variations and modifications without departing from the spirit and scope of the invention. All such variations and modifications, including those discussed above, are intended to be included within the scope of the invention as defined in the appended claims.

We claim:

1. An implant inserter device, comprising an outer collar having a proximal end, a distal end, an aperture extending from said proximal end to said distal end, an interior surface, and a plurality of cammed surfaces formed on said interior surface extending proximate from said distal end; an inner sleeve having a proximal end, a distal end, an aperture extending from said proximal end of said inner sleeve to said distal end of said inner sleeve, an exterior surface, and a plurality of ribs projecting outwardly from said exterior surface proximate to said distal end of said inner sleeve, said inner sleeve being slidably and rotatably received within said aperture of said outer collar such that said inner sleeve and said outer collar are arranged substantially coaxially relative to each other, each of said plurality of ribs being releasably engageable with a corresponding one of said plurality of cammed surfaces when said inner sleeve is rotated relative to said outer collar, whereby when said plurality of ribs releasably engages said plurality of cammed surfaces, said distal end of said inner sleeve collapses from an undeformed position, in which said distal end of said inner sleeve does not grip an implant housed within said inner sleeve proximate to said distal end of said inner sleeve, and a deformed position, in which said distal end of said inner sleeve grips the implant; and a push rod slidably received within said aperture of said inner sleeve, said push rod being movable between an extended position and a retracted position.

2. The implant inserter device as claimed in claim 1, wherein said inner sleeve includes a retaining groove formed circumferentially within said exterior surface of said inner sleeve, and said outer collar includes a least one hook member extending outwardly from and circumferentially on said interior surface of said outer collar, said at least one hook member engages said retaining groove to removably and rotatably interlock said inner sleeve and said outer collar with one another.

3. The implant inserter device as claimed in claim 2, wherein said proximal end of said outer collar includes a slot having a pair of opposing end walls, and said inner sleeve includes a stop member extending outwardly from said exterior surface of said inner sleeve, said stop member being received within said slot, whereby said stop member limits the rotation of said inner sleeve relative to said outer collar when said stop member travels within said slot from one of said end walls to the other of said end walls.

4. The implant inserter device as claimed in claim 3, wherein said inner sleeve includes a first portion positioned at said proximal end of said inner sleeve, and an elongated tubular member that extends from said first portion to said distal end of said inner sleeve, said tubular member being sheathed within said aperture of said outer collar, and said first portion being exposed from said outer collar.

5. The implant inserter device as claimed in claim 4, wherein said outer collar includes an exterior surface and first gripping means positioned on said exterior surface of said outer collar, and said inner sleeve includes second gripping means positioned on said exterior surface of said first portion of said inner sleeve, said first and second gripping means facilitating the rotation of said inner sleeve relative to said outer collar.

6. The implant inserter device as claimed in claim 5, wherein said first gripping means includes a first pair of diametrically opposed fins extending outwardly from said exterior surface of said outer collar, and said second gripping means includes a second pair of diametrically opposed fins extending outwardly from said exterior surface of said first portion of said inner sleeve.

7. The implant inserter device as claimed in claim 6, wherein one of said first pair of fins is aligned longitudinally with one of said second pair of fins, and the other of said first pair of fins is aligned longitudinally with the other of said second pair of fins when said distal end of said inner sleeve is in its said undeformed position.

8. The implant inserter device as claimed in claim 6, wherein said first pair of fins extends in a first plane and said second pair of fins extends in a second plane when said distal end of said inner sleeve is in its said deformed position, said first plane being substantially perpendicular to said second plane.

9. The implant inserter device as claimed in claim 6, wherein said tubular member includes a wall thickness that decreases from said proximal end of said inner sleeve to said distal end of said inner sleeve.

10. The implant inserter device as claimed in claim 9, wherein said tubular member is made from a substantially soft and flexible material.

11. The implant inserter device as claimed in claim 10, wherein said push rod urges the implant through said tubular member of said inner sleeve when said push rod is moved from its retracted position to its extended position.

12. The implant inserter device as claimed in claim 5, wherein each of said first and second gripping means includes a plurality of ribs.

13. The implant inserter device as claimed in claim 5, wherein each of said first and second gripping means includes a plurality of raised beads.

14. The implant inserter device as claimed in claim 5, wherein each of said first and second gripping means includes an overmolded portion.

15. The implant inserter device as claimed in claim 1, wherein said inner sleeve is made from a translucent material and said outer collar is made from an opaque material.

16. The implant inserter device as claimed in claim 1, wherein said inner sleeve and said outer collar are each made from an opaque material.

17. The implant inserter device as claimed in claim 1, wherein said inner sleeve is made from a translucent material and said outer collar is made from a transparent material.

* * * * *